(12) United States Patent
Rosani et al.

(10) Patent No.: US 10,259,185 B2
(45) Date of Patent: Apr. 16, 2019

(54) METHOD AND UNIT FOR MAKING SECTIONS OF PADDING FOR ABSORBENT SANITARY ARTICLES

(75) Inventors: Marco Rosani, Vailate (IT); Matteo Piantoni, Albino (IT); Diego Sacchi, Capralba (IT); Gabriele Pastrello, Milan (IT); Alberto Perego, Milan (IT)

(73) Assignee: GDM S.P.A., Bologna (IT)

( * ) Notice: Subject to any disclaimer, the term of this patent is extended or adjusted under 35 U.S.C. 154(b) by 624 days.

(21) Appl. No.: 14/009,926

(22) PCT Filed: Mar. 27, 2012

(86) PCT No.: PCT/IB2012/051459
§ 371 (c)(1),
(2), (4) Date: Oct. 4, 2013

(87) PCT Pub. No.: WO2012/137100
PCT Pub. Date: Oct. 11, 2012

(65) Prior Publication Data
US 2014/0024514 A1 Jan. 23, 2014

(30) Foreign Application Priority Data
Apr. 8, 2011 (IT) .............................. BO2011A0186

(51) Int. Cl.
*B31D 1/00* (2017.01)
*A61F 13/15* (2006.01)

(52) U.S. Cl.
CPC ...... *B31D 1/0075* (2013.01); *A61F 13/15617* (2013.01); *A61F 13/15666* (2013.01); *A61F 13/15699* (2013.01)

(58) Field of Classification Search
CPC .......... A61F 13/15577; A61F 13/15699; A61F 13/15617; A61F 13/15666; A61F 13/15634; A61F 13/1565; B31F 1/0075
(Continued)

(56) References Cited

U.S. PATENT DOCUMENTS

| 1,680,268 A | * | 8/1928 | Weiss ............... A61F 13/15666 19/145 |
| 4,372,312 A | * | 2/1983 | Fendler ................. A61F 13/535 604/370 |

(Continued)

FOREIGN PATENT DOCUMENTS

| EP | 2609899 A1 | 7/2013 |
| GB | 2286832 | 8/1995 |

(Continued)

OTHER PUBLICATIONS

International Search Report dated May 22, 2012 from counterpart PCT App No. PCT/IB2012/051459.

(Continued)

*Primary Examiner* — Alexander M Valvis
*Assistant Examiner* — Lucas E. A. Palmer
(74) *Attorney, Agent, or Firm* — Shuttleworth & Ingersoll, PLC; Timothy Klima

(57) ABSTRACT

In a unit for making sections of padding for absorbent sanitary articles comprising a first rotary conveyor for feeding and forming a continuous succession of outer pads, comprising at least one layer, a second rotary conveyor for feeding and forming a continuous succession of inner pads comprising two layers, a third rotary conveyor for the pads defining a position for superposing the outer pads and the inner pads, there are compressing means for the two-layer inner pads upstream of the superposing position and second compressing means for the superposed pads downstream of the superposing position.

25 Claims, 3 Drawing Sheets

(58) Field of Classification Search
USPC .......................................................... 493/381
See application file for complete search history.

(56) References Cited

U.S. PATENT DOCUMENTS

| | | | | |
|---|---|---|---|---|
| 4,598,441 | A * | 7/1986 | Stemmler | A61F 13/15626 19/145 |
| 4,806,408 | A * | 2/1989 | Pierre | A61F 13/4702 428/138 |
| 4,886,632 | A * | 12/1989 | Van Iten | A61F 13/15577 156/252 |
| 4,908,175 | A * | 3/1990 | Angstadt | A61F 13/15585 264/113 |
| 5,030,314 | A * | 7/1991 | Lang | A61F 13/15634 156/390 |
| 5,128,082 | A * | 7/1992 | Makoui | A61F 13/15642 264/112 |
| 5,135,521 | A * | 8/1992 | Luceri | A61F 13/512 428/137 |
| 5,447,677 | A * | 9/1995 | Griffoul | A61F 13/15658 264/113 |
| 5,593,399 | A * | 1/1997 | Tanzer | A61F 13/5323 604/358 |
| 5,609,588 | A * | 3/1997 | DiPalma | A61F 13/15203 428/332 |
| 5,643,240 | A * | 7/1997 | Jackson | A61F 13/512 604/366 |
| 5,803,920 | A * | 9/1998 | Gilman | A61F 13/15203 604/378 |
| 5,925,439 | A * | 7/1999 | Haubach | A61F 13/5323 428/178 |
| 6,060,638 | A * | 5/2000 | Paul | A61F 13/15203 604/367 |
| 6,220,999 | B1 * | 4/2001 | Kugler | A61F 13/15626 493/256 |
| 6,652,798 | B1 * | 11/2003 | Edvardsson | A61F 13/15658 264/112 |
| 6,706,129 | B2 * | 3/2004 | Ando | A61F 13/15658 156/209 |
| 7,619,131 | B2 * | 11/2009 | Soerens | A61F 13/15203 526/218.1 |
| 7,803,244 | B2 * | 9/2010 | Siqueira | A61F 13/4902 156/229 |
| 7,981,355 | B2 * | 7/2011 | Edvardsson | A61F 13/15626 264/299 |
| 8,057,620 | B2 | 11/2011 | Perego et al. | |
| 8,178,035 | B2 * | 5/2012 | Edvardsson | A61F 13/15626 264/299 |
| 8,182,736 | B2 * | 5/2012 | Edvardsson | A61F 13/15626 264/299 |
| 9,248,608 | B2 * | 2/2016 | Ogasawara | A61F 13/15658 |
| 2002/0056516 | A1 * | 5/2002 | Ochi | A61F 13/15634 156/293 |
| 2002/0095127 | A1 * | 7/2002 | Fish | A61F 13/5323 604/368 |
| 2004/0061264 | A1 * | 4/2004 | Heyn | A61F 13/15203 264/518 |
| 2004/0122394 | A1 * | 6/2004 | Fell | A61F 13/15634 604/378 |
| 2005/0113791 | A1 * | 5/2005 | Neubauer | A61F 13/15617 604/387 |
| 2006/0021695 | A1 * | 2/2006 | Blessing | A61F 13/15658 156/196 |
| 2006/0048880 | A1 * | 3/2006 | Blessing | A61F 13/15658 156/60 |
| 2006/0069372 | A1 * | 3/2006 | Chakravarty | A61F 13/15617 604/385.02 |
| 2007/0027435 | A1 * | 2/2007 | Nakagawa | A61F 13/15203 604/368 |
| 2010/0001426 | A1 * | 1/2010 | Edvardsson | A61F 13/15617 264/113 |
| 2010/0032860 | A1 * | 2/2010 | Hernandez | A61F 13/15617 264/175 |
| 2010/0051166 | A1 * | 3/2010 | Hundorf | A61F 13/15658 156/62.8 |
| 2010/0249737 | A1 * | 9/2010 | Ito | A61F 13/15634 604/367 |
| 2011/0162989 | A1 * | 7/2011 | Ducker | A61F 13/5323 206/389 |
| 2012/0041405 | A1 * | 2/2012 | Alkmin | A61F 13/15626 604/383 |
| 2012/0296294 | A1 * | 11/2012 | Hashimoto | A61F 13/531 604/367 |
| 2013/0240125 | A1 * | 9/2013 | Nelson | A61F 13/15699 156/182 |
| 2013/0267924 | A1 * | 10/2013 | Mukai | A61F 13/533 604/374 |
| 2015/0126949 | A1 * | 5/2015 | Ashraf | A61F 13/15617 604/372 |

FOREIGN PATENT DOCUMENTS

| | | |
|---|---|---|
| GB | 2286832 A | 8/1995 |
| JP | 2009507542 A | 2/2009 |
| JP | 2012143539 A | 8/2012 |
| WO | 2007/029115 | 3/2007 |
| WO | WO2007029115 A1 | 3/2007 |
| WO | WO2008010754 A1 | 1/2008 |
| WO | WO2012086210 A1 | 6/2012 |

OTHER PUBLICATIONS

Summary Translation of Japanese Office Action dated May 17, 2016 for counterpart Japanese Application No. 2014-503241.
D3—Opposition Documents from GDM S.p.A. Opposition to Curt G Joa, Inc. Patent No. EP2609899 dated Jul. 22, 2015.
D4—GDM Invoice No. 909/VI dated Oct. 25, 2001 to SCA Hygiene Products Gennep B.V.
D5—GDM Invoice No. 829/VI dated Dec. 10, 2004 to SCA Hygiene Products Gennep B.V.
D6—GDM Invoice No. 648/VI dated Jul. 30, 2009 to SCA Hygiene Products Gennep B.V.
D7—Excerpt from GDM Operating and Maintenance Manual "Production of Adult Diaper Machine" AT 450 NEOS 3 Flex Adult, Manual No. D0000511, Revision: Jul. 23, 2009, Year of Manufacture: 2009, Serial No. A0AT080951M1.
Opposition Documents from Curt G Joa, Inc. Opposition to GDM S.p.A. Patent No. EP2694006 filed Oct. 28, 2015.
Japanese Office Action dated Apr. 25, 2017 from counterpart Japanese App No. 2014-503241.

* cited by examiner

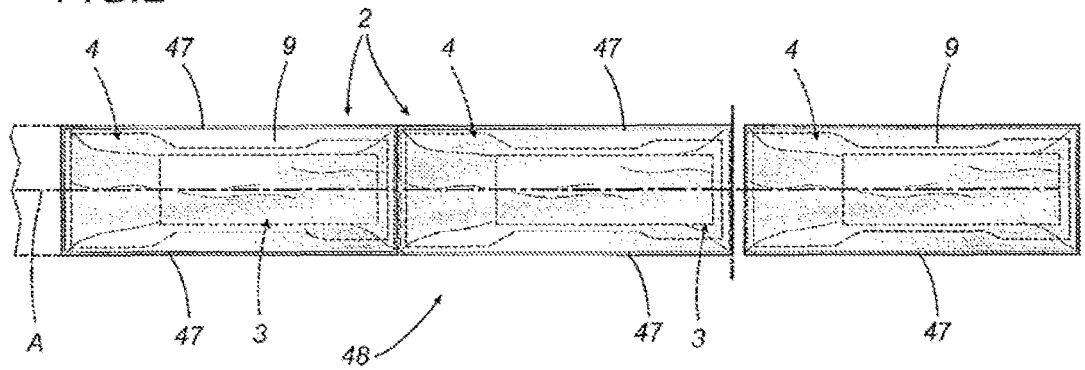
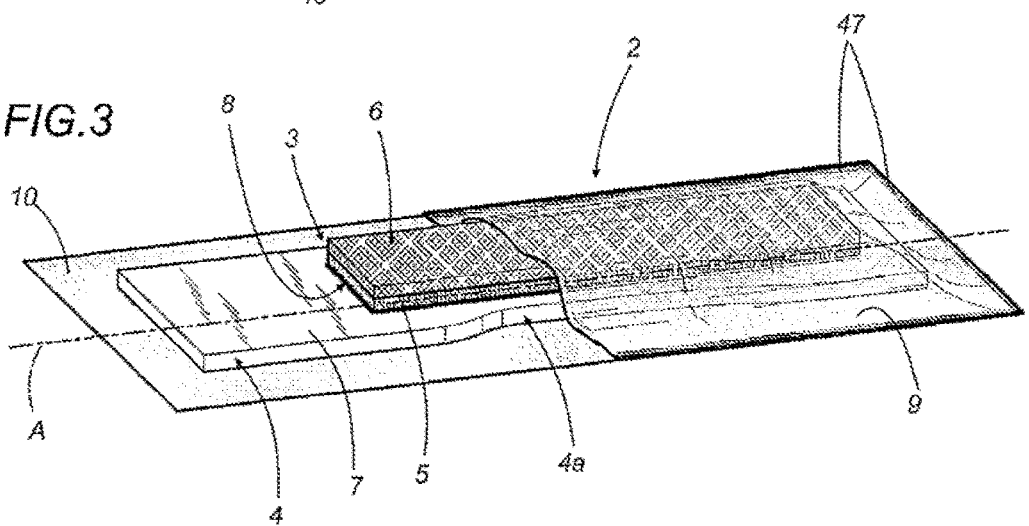
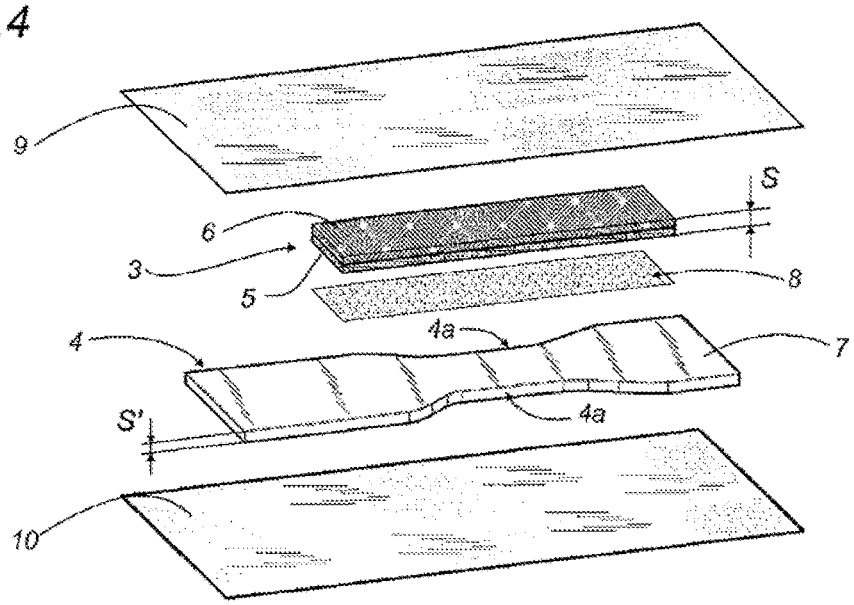

METHOD AND UNIT FOR MAKING SECTIONS OF PADDING FOR ABSORBENT SANITARY ARTICLES

This application is the National Phase of International Application PCT/IB2012/051459 filed Mar. 27, 2012 which designated the U.S. and that International Application was published under PCT Article 21(2) in English.

This application claims priority to Italian Patent Application No. BO2011A000186 filed Apr. 8, 2011, which application is incorporated by reference herein.

TECHNICAL FIELD

This invention relates to a method and a unit for making sections of padding for absorbent sanitary articles.

In particular, this invention relates to a method and a unit for making sections of padding for absorbent sanitary articles such as nappies for babies, incontinence pads for adults, sanitary towels and the like.

BACKGROUND ART

As is known, such articles are obtained by superposing a sheet of permeable material (non-woven fabric) on a sheet of impermeable material, and interposing between them a section of padding comprising an absorbent pad.

In recent years, to increase the absorbency of such products, manufacturers have made a section of padding consisting of at least two superposed pads having different shapes and dimensions.

In general, a first pad, or inner pad, which is substantially rectangular, is positioned on a second supporting pad, or outer pad, which is larger, having a substantially hourglass anatomical shape.

Usually, both pads are made from a mixture consisting of cellulose pulp (fluff) and granules of superabsorbent polymers (SAP), In order to increase drainage of the liquid absorbed and to increase the concentration of the superabsorbent polymer in a precise zone of the section of padding, the inner pad is made thicker than the supporting pad, by superposing two or more layers of absorbent material containing a large quantity of granular superabsorbent material (SAP).

In a prior art machine for making a section of padding of the above-mentioned type, there is a first suction drum for forming and conveying the multi-layer inner pad and a second suction drum for forming and conveying the outer supporting pad, which consists of a single layer of absorbent material.

The first and second drums are side by side and rotate in opposite directions about respective axes which are parallel with each other. The two drums are substantially at a tangent to one another at a station where the multi-layer inner pad, conveyed by the first drum, is placed on the outer pad, conveyed by the second drum.

Then, the two superposed pads are conveyed towards compressing means to complete the production of the absorbent section of padding.

It has been noticed that the absorbent section of padding, made according to the prior art described, may not be suitably stuck together and compact, despite the above-mentioned compressing operation, since the granules of superabsorbent material (SAP), present in a large quantity in the layers which make up the multi-layer inner pad, do not allow the fibres of the cellulose pulp (fluff) to stably interpenetrate one another.

A lack of cohesion between the layers which make up the multi-layer pad results in dispersion in the environment of the granules of superabsorbent material (SAP), which, over time, may cause incorrect operation or faults in the mechanical devices for forming the pads.

Moreover, in the prior art referred to the absorbent section of padding may be unevenly compressed, since the compression occurs on superposed pads with different thicknesses.

DISCLOSURE OF THE INVENTION

The aim of this invention is to provide a unit for making sections of padding for absorbent sanitary articles which have greater cohesion and compactness, and a method for making such sections of padding.

The technical purpose indicated and the aims specified are achieved by a method and a unit comprising features described herein.

BRIEF DESCRIPTION OF THE DRAWINGS

Further features and advantages of this invention are more apparent in the non-limiting description which follows of a preferred, non-limiting embodiment of a unit, illustrated in the accompanying drawings, in which:

FIG. 2 is a scaled-up view of a detail from FIG. 1;

FIG. 3 is a perspective view of the section of padding made by the unit of FIG. 1;

FIG. 4 is an exploded view of the section of padding illustrated in FIG. 3; and

With reference to FIG. 1, the numeral 1 denotes in its entirety a unit for making sections of padding 2 for absorbent sanitary articles.

DETAILED DESCRIPTION OF THE PREFERRED EMBODIMENTS OF THE INVENTION

Figure 1:
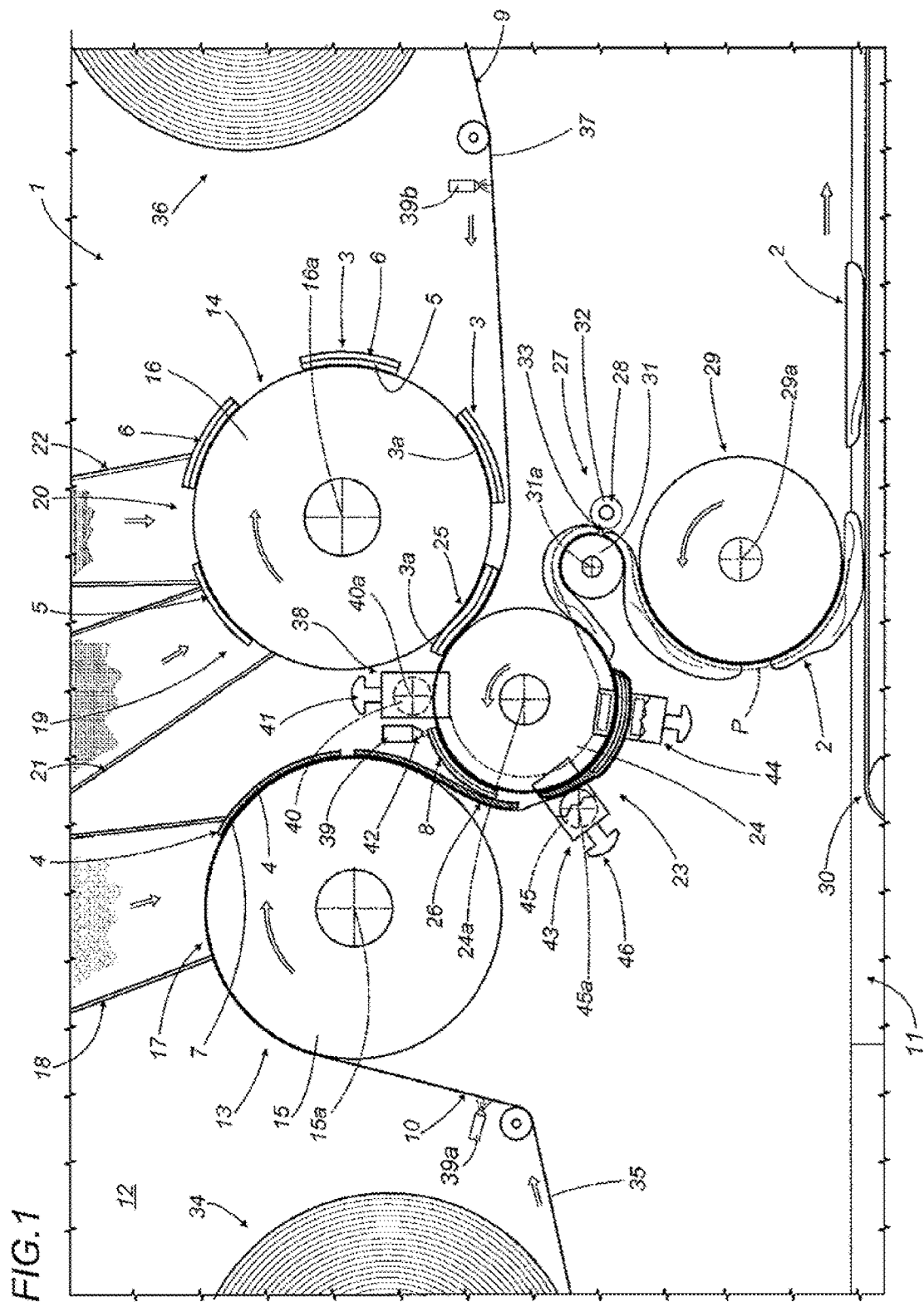
FIG. 1 is a schematic front view of a unit for making sections of padding for absorbent sanitary articles.

With reference to FIGS. 3 and 4, the section of padding 2 has a substantially rectangular shape, extending along an axis A, and comprises a first pad 3, hereinafter referred to more precisely as the inner pad 3, and a second pad, hereinafter referred to as the outer pad 4, both made of absorbent material, the pads being superposed.

The inner pad 3, thus named because in practice it faces towards the user, has smaller longitudinal and transversal dimensions than the outer pad.

In the example shown the inner pad 3 has the shape of a rectangle.

The outer pad 4, thus named because it is furthest from the user, supports the inner pad 3 and is laterally provided with two recesses 4a, symmetrical relative to the axis A, so that it has a substantially hourglass anatomical shape.

According to alternative embodiments not illustrated, the outer pad 4 is without the two recesses 4a.

The inner pad 3 of the section of padding 2 comprises at least one layer of absorbent material. In particular, according to the embodiment described, the inner pad 3 comprises two layers or panels 5 and 6 of absorbent material.

Preferably, the panel 5 and/or the panel 6 contain cellulose fibres (fluff) and/or granular superabsorbent material (SAP).

Similarly, the outer pad 4 comprises at least one panel or layer 7 of absorbent material. It should be noticed that, unlike the inner pad 3, in the example shown the outer pad 4 comprises a single layer 7 of absorbent material.

Preferably, the panel 7 also contains cellulose fibres (fluff) and/or granular superabsorbent material (SAP).

As described, the inner pad 3 has a thickness S which is greater than the thickness S' of the outer pad 4.

Interposed between the two pads 3 and 4 there may be a layer of adhesive substance, labelled 8.

The two pads 3 and 4 are enclosed between two sheets 9 and 10 of permeable or hydrophilic filter material, which are sealed together at their rectangular edges.

The unit 1 comprises a base 11 delimited at the front by a vertical wall 12, forming the support for a plurality of conveyors and transfer means which are mounted on axes transversal to the wall 12.

The unit 1 comprises a first rotary conveyor 13 for forming and feeding a continuous succession of the outer pads 4 of absorbent material and a second rotary conveyor 14 for forming and feeding a continuous succession of the inner pads 3, comprising two superposed layers 5 and 6 of absorbent material.

The conveyors 13 and 14 respectively comprise a first roller 15 and a second roller 16, both rotating clockwise (observing FIG. 1) about respective axes 15a and 16a which are parallel with each other and positioned in the same horizontal plane.

Above the first roller 15, in a zone 17 for forming the outer pad 4, there is a hopper 18 for feeding absorbent material comprising a mixture of cellulose fibres (fluff) and granules of superabsorbent material (SAP).

If, not illustrated, the outer pad 4 is a multi-layer pad, alongside the hopper 18 there is a further hopper similar to the hopper 18. The further hopper provided if necessary feeds absorbent material comprising cellulose fibres (fluff) and/or granules of superabsorbent material (SAP).

Above the second roller 16, in two zones, from left to right labelled 19 and 20 and for forming the two layers 5 and 6 of the inner pad 3, there are respective hoppers 21 and 22.

More precisely, the hopper 21 feeds absorbent material comprising cellulose fibres (fluff) for forming the layer 5, while the hopper 22 feeds a mixture of cellulose fibres (fluff) and granules of superabsorbent material (SAP) for forming the second layer 6.

The cylindrical surfaces of the roller 15 and the roller 16 are equipped with suction holders, not illustrated, spaced at equal angles, designed to receive and retain by suction respectively the outer pads 4 and the inner pads 3.

The numeral 23 denotes a third conveyor, comprising a third roller 24 rotating anti-clockwise about an axis 24a positioned below the axes 15a and 16a and equidistant from them.

The third roller 24 is substantially at a tangent to the second roller 16 at a position 25 for receiving the inner pads 3 and to the first roller 15 at a position 26 for receiving the outer pads 4 and for superposing the latter and the inner pads 3. With reference to the direction of rotation of the third roller 24, the receiving position 25 is located upstream of the receiving and superposing position 26.

The third roller 24 is part of the means, labelled 27 as a whole, for transferring the sections of padding 2 to a line, not illustrated, for making absorbent sanitary articles.

The transfer means 27 extend along a path P and comprise, in addition to the third roller 24, a cutting device 28, located, relative to the roller 24, in a position substantially opposite the first roller 15, a spacer roller 29, rotating about an axis 29a, and a conveyor 30 for feeding to the line for making absorbent sanitary articles.

The cutting device 28 comprises a suction roller 31 rotating clockwise about an axis 31a and a roller 32 equipped with a blade 33 which operates in conjunction with the roller 31.

The numeral 34 denotes means for feeding a first continuous web 35 of permeable or hydrophilic filter material, on the cylindrical surface of the first roller 15, upstream of the zone 17 for forming the outer pad 4.

The numeral 36 denotes means for feeding a second continuous web 37 of permeable or hydrophilic filter material, on the cylindrical surface of the third roller 24, immediately upstream of the tangent zone 25 between the second roller 16 and the third roller 24.

In practice, during rotation of the first roller 15, at the hopper 18 outlet zone 17, the outer pads 4 are gradually formed one after another in the holders, not illustrated, on top of the web 35.

The roller 15 uses suction to retain the outer pads 4 and transfers them from the forming zone 17 towards the position 26.

Before receiving the outer pads 4 the web 5 is provided with an adhesive substance by a unit 39a for application of an adhesive.

Similarly, during rotation of the second roller 16, at the hopper 21 outlet zone 19, the layers 5 are gradually formed one after another, and at the second hopper 22 outlet zone 20 the second layers 6 of the inner pads 3 are gradually formed one after another on top of the layers 5.

The second roller 16 uses suction to retain the inner pads 3 and transfers them from the forming zone 20 towards the tangent position 25, where they are transferred onto the cylindrical surface of the third roller 24 with the second web 37 interposed between the pads and the third roller.

Before receiving the inner pads 3 the web 37 is provided with an adhesive substance by a unit 39b for application of an adhesive. According to an alternative embodiment not illustrated, the unit 39b for application of an adhesive is absent.

The third roller 24 transfers the pads 3 comprising two layers 5 and 6 from the position 25 to the position 26, through compressing means 38.

If the layer 8 of adhesive substance must be interposed between the pads 3 and 4, the pads 3 are subjected to the action of a unit 39c for application of an adhesive between the compressing means 38 and the position 26. According to another alternative embodiment not illustrated, the pads 4 are subjected to the action of a unit for application of an adhesive which is interposed between the hopper 18 and the position 26.

The compressing means 38 comprise a roller 40, idly rotating about an axis 40a parallel with the axis 24a and operating in conjunction with the third roller 24 so as to compress the two superposed layers 5 and 6 of absorbent material, in such a way as to compact them, reducing the thickness S of the inner pad 3.

There are pneumatic means 41 acting on the shaft of the roller 40 for varying the distance between the cylindrical surfaces of the rollers 40 and 24 and for applying, in that way, a compression force on the layers 5 and 6 of the inner pad 3.

At the superposing position 26, the outer pad 4, fed by the roller 15, is superposed on the inner pad 3 comprising two layers 5 and 6, fed by the roller 16.

Downstream of the superposing position 26, the two pads 3 and 4, superposed and enclosed between the webs 35 and 37, are transferred along the path P, through the second compressing means 43 and a sealing device 44.

The second compressing means 43 are the same as the first compressing means 38 and simultaneously compress the two superposed pads 3 and 4 enclosed between the webs 35 and 37.

Downstream of the second compressing means 43, in the direction of rotation of the third roller 24, the device 44 seals the two continuous webs 35 and 37 substantially along the entire border 47 of each outer pad 4 having the larger dimensions.

With reference to FIG. 2, at the outfeed of the roller 24, the continuous succession of sections of padding 2, labelled 48, is divided into pieces by the cutting device 28, to form the individual sections of padding 2.

At the cutting device 28 outfeed, the spacer roller 29 picks up the individual sections of padding 2 and, according to a known method, places them spaced out by a predetermined step on the conveyor 30 which feeds the line for making absorbent sanitary articles, not illustrated.

It is evident from the above description how the various disadvantages, highlighted in the introduction with reference to the prior art, are eliminated according to this invention.

The operation compressing the multi-layer inner pad 3 eliminates the disadvantages caused by the dispersion of particles of superabsorbent material.

Moreover, said compression significantly reduces the thickness S of the inner pad 3 and together with the final compression of the two superposed pads 3 and 4, results in improved compacting of the section of padding 2 and a reduction in its overall dimensions.

Figure 5:
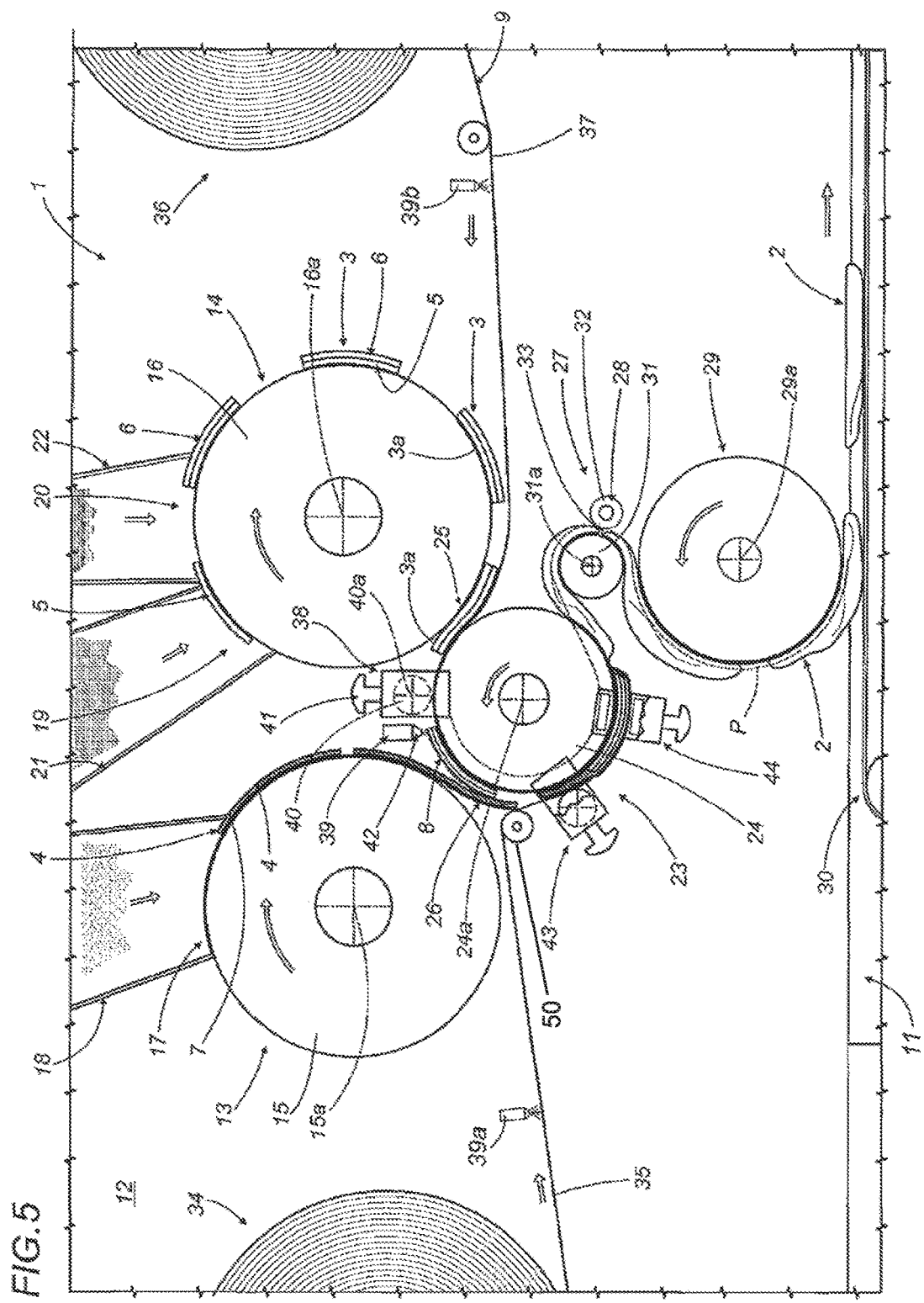
FIG. 5 illustrates an alternative embodiment, of the unit of FIG. 1.

FIG. 5 shows an alternative embodiment of what is described above, according to which the web 35 is not wound around the roller 15, but around a small return roller 50 located at the position 26.

The invention claimed is:

1. A method for making sections of padding for absorbent sanitary articles comprising:
   forming on a first conveyor a continuous succession of single discrete outer pads comprising at least one panel or layer of absorbent material;
   forming on a second conveyor a continuous succession of single discrete inner pads comprising at least one panel or layer of absorbent material;
   superposing each outer pad on an inner pad to make assembled pads comprising multiple layers of absorbent material;
   feeding the assembled pads comprising multiple layers to a production line for absorbent sanitary articles;
   compressing the inner pads to decrease an overall thickness of the inner pads before the superposing the inner pads on the outer pads;
   wherein the superposing each outer pad on the inner pad is carried out on a third rotary conveyor by positioning the inner pad on the third rotary conveyor and superposing the outer pad over the inner pad on the third rotary conveyor, the third rotary conveyor separate from both the first conveyor and the second conveyor;
   wherein the feeding the assembled pads comprising multiple layers to the production line is carried out on the third rotary conveyor.

2. The method according to claim 1, wherein the inner pads comprise two or more superposed layers of absorbent material.

3. The method according to claim 1, and further comprising compressing the assembled pads.

4. The method according to claim 1, and further comprising: feeding to the first rotary conveyor, upstream of a forming zone for the outer pad, a first continuous web of permeable or hydrophilic filter material; feeding to the third rotary conveyor, upstream of a receiving zone for the inner pads, a second continuous web of permeable or hydrophilic filter material; after superposing the outer pads on the inner pads, the assembled pads being enclosed between the two continuous webs.

5. The method according to claim 1, and further comprising sealing together the webs along an entire border of each outer pad, and cutting into pieces the continuous webs, thus making individual sections of padding.

6. The method according to claim 1, and further comprising applying a layer of adhesive substance to at least one chosen from the inner pads, the outer pads, the first continuous web of permeable or hydrophilic filter material and the second continuous web of permeable or hydrophilic filter material.

7. A unit for making sections of padding for absorbent sanitary articles comprising:
   a first rotary conveyor for feeding and forming a continuous succession of single discrete outer pads comprising at least one layer of absorbent material,
   a second rotary conveyor for feeding and forming a continuous succession of single discrete inner pads comprising at least one layer of absorbent material,
   wherein each outer pad is superposed on a respective inner pad at a superposing position to make assembled pads comprising multiple layers of absorbent material,
   a transfer device including a third rotary conveyor substantially tangent to the first rotary conveyor and the second rotary conveyor, the third rotary conveyor having a second input position adjacent an output position of the second rotary conveyor for receiving the inner pads from the second rotary conveyor and a first input position adjacent an output position of the first rotary conveyor for receiving the outer pads from the first rotary conveyor and for transferring the assembled pads along a path to a production line for absorbent sanitary articles,
   a compressing device including a compressing surface for compressing the inner pads to decrease an overall thickness of the inner pads upstream of the superposing position;
   wherein the superposing position is defined by a tangent zone between the first rotary conveyor and the third rotary conveyor and wherein the third rotary conveyor is separate from both the first rotary conveyor and the second rotary conveyor.

8. The unit according to claim 7, wherein the inner pads comprise two or more superposed layers of absorbent material.

9. The unit according to claim 7, and further comprising a second compressing device including a second compressing surface for compressing the assembled pads downstream of the superposing position.

10. The unit according to claim 7, and further comprising means for feeding a first continuous web of permeable or hydrophilic filter material to the first conveyor upstream of a forming zone for the outer pad, and means for feeding a second continuous web of permeable or hydrophilic filter material to the third rotary conveyor upstream of the tangent zone between the third rotary conveyor and the second conveyor; after superposing the outer pads on the inner pads, the assembled pads being enclosed between the two continuous webs.

11. The unit according to claim 7, and further comprising means for applying an adhesive substance to at least one chosen from the inner pads, the outer pads, the first continuous web of permeable or hydrophilic filter material and the second continuous web of permeable or hydrophilic filter material.

12. The unit according to claim 7, and further comprising a sealing device for sealing together the two continuous webs downstream of the superposing position.

13. The unit according to claim 12, wherein the compressing device for the inner pads, the second compressing device for the assembled pads and the sealing device operate in conjunction with the third rotary conveyor, and with the compressing device, the second compressing device and the sealing device facing a periphery of the third rotary conveyor.

14. The unit according to claim 7, wherein the transfer device comprises a cutting device for cutting into pieces the continuous webs, thus making individual sections of padding.

15. The unit according to claim 7, wherein the transfer device comprises, interposed between the cutting device and the production line for absorbent sanitary articles, a spacer roller for the sections of padding.

16. A unit for making sections of padding for absorbent sanitary articles comprising:
   a first rotary conveyor for feeding and forming a continuous succession of single discrete outer pads comprising at least one layer of absorbent material,
   a second rotary conveyor for feeding and forming a continuous succession of single discrete inner pads comprising at least one layer of absorbent material,
   wherein each outer pad is superposed on a respective inner pad at a superposing position to make assembled pads comprising multiple layers of absorbent material,
   a transfer conveyor including a third rotary conveyor substantially tangent to the first rotary conveyor and the second rotary conveyor, the third rotary conveyor having a second input position adjacent an output position of the second rotary conveyor for receiving the inner pads from the second rotary conveyor and a first input position adjacent an output position of the first rotary conveyor for receiving the outer pads from the first rotary conveyor and for transferring the assembled pads along a path to a production line for absorbent sanitary articles,
   a compressing device including a compressing surface compressing the inner pads to decrease an overall thickness of the inner pads upstream of the superposing position;
   wherein the superposing position is defined by a tangent zone between the first rotary conveyor and the third rotary conveyor and wherein the third rotary conveyor is separate from both the first rotary conveyor and the second rotary conveyor.

17. The unit according to claim 16, wherein the inner pads comprise two or more superposed layers of absorbent material.

18. The unit according to claim 16, and further comprising a second device including a compressing surface compressing the assembled pads downstream of the superposing position.

19. The unit according to claim 18, and further comprising:
   a first feed conveyor for feeding a first continuous web of permeable or hydrophilic filter material to the first conveyor upstream of a forming zone for the outer pad, and
   a second feed conveyor for feeding a second continuous web of permeable or hydrophilic filter material to the third rotary conveyor upstream of the tangent zone between the third rotary conveyor and the second conveyor; after superposing the outer pads on the inner pads, the assembled pads being enclosed between the two continuous webs.

20. The unit according to claim 16, and further comprising an adhesive applicator for applying an adhesive substance to at least one chosen from the inner pads, the outer pads, the first continuous web of permeable or hydrophilic filter material and the second continuous web of permeable or hydrophilic filter material.

21. The unit according to claim 16, and further comprising a sealing device for sealing together the two continuous webs downstream of the superposing position.

22. The unit according to claim 21, wherein the compressing device for the inner pads and the second compressing device for the assembled pads operate in conjunction with the third rotary conveyor, and with the compressing device, the second compressing device facing a periphery of the third rotary conveyor.

23. The unit according to claim 22, wherein the sealing device operates in conjunction with the third rotary conveyor; the sealing device facing a periphery of the third rotary conveyor downstream of the second compressing device.

24. The unit according to claim 16, wherein the transfer conveyor comprises a cutting device including a blade for cutting into pieces the continuous webs, thus making individual sections of padding.

25. The unit according to claim 16, wherein the transfer conveyor comprises, interposed between the cutting device and the production line for absorbent sanitary articles, a spacer roller for the sections of padding.

* * * * *